(12) United States Patent
Judson

(10) Patent No.: US 11,786,660 B2
(45) Date of Patent: Oct. 17, 2023

(54) INJECTION DEVICE WITH PLUNGER ARRANGMENT AND CONVERGING RAMPS

(71) Applicant: Eli Lilly and Company, Indianapolis, IN (US)

(72) Inventor: Jared Alden Judson, Medford, MA (US)

(73) Assignee: Eli Lilly and Company, Indianapolis, IN (US)

(*) Notice: Subject to any disclaimer, the term of this patent is extended or adjusted under 35 U.S.C. 154(b) by 908 days.

(21) Appl. No.: 16/608,210

(22) PCT Filed: Apr. 25, 2018

(86) PCT No.: PCT/US2018/029331
§ 371 (c)(1),
(2) Date: Oct. 25, 2019

(87) PCT Pub. No.: WO2018/204144
PCT Pub. Date: Nov. 8, 2018

(65) Prior Publication Data
US 2020/0188595 A1    Jun. 18, 2020

Related U.S. Application Data

(60) Provisional application No. 62/500,055, filed on May 2, 2017.

(51) Int. Cl.
*A61M 5/24* (2006.01)
*A61M 5/315* (2006.01)

(52) U.S. Cl.
CPC .......... *A61M 5/24* (2013.01); *A61M 5/31501* (2013.01); *A61M 5/3158* (2013.01);
(Continued)

(58) Field of Classification Search
CPC .. A61M 5/24; A61M 5/31501; A61M 5/3158; A61M 2005/2407;
(Continued)

(56) References Cited

U.S. PATENT DOCUMENTS

| 5,084,017 A | 1/1992 | Maffetone |
| 2007/0167912 A1 | 7/2007 | Causey |

(Continued)

FOREIGN PATENT DOCUMENTS

| EP | 2438946 | 4/2012 |
| FR | 2714824 | 7/1995 |

(Continued)

OTHER PUBLICATIONS

International Search Report of the International Searching Authority pertaining to International Application No. PCT/US2018/029331; dated Aug. 6, 2018.

(Continued)

*Primary Examiner* — Amber R Stiles
(74) *Attorney, Agent, or Firm* — Jonathan Anderson

(57) ABSTRACT

An injection device is disclosed including a housing assembly defining a pair of ramps and adapted to hold a medicament cartridge. A driver is adapted to advance the piston within the cartridge. A plunger having a pair of arms is moveable between a retracted position and an advanced position. Each of the arms are engageable with a respective one of the ramps as the plunger is advanced. A braking mechanism may include braking members on the arms and braking tracks proximate the ramps. Excessive force exerted on the plunger may flex the arms and engage the braking members with the braking tracks. The plunger arms may be connected together by a material bridge that biases the plunger arms apart from each other. The arms may include detents that engage to prevent the arms from moving due to (Continued)

the biasing force of the material bridge when the arms are in the fully retracted position.

16 Claims, 10 Drawing Sheets

(52) U.S. Cl.
CPC ............... *A61M 2005/2407* (2013.01); *A61M 2005/31508* (2013.01); *A61M 2205/581* (2013.01)

(58) Field of Classification Search
CPC .. A61M 2005/31508; A61M 2205/581; A61M 2005/2477; A61M 2005/3143; A61M 5/3146; A61M 2005/2411; A61M 2005/2418; A61M 2005/2488
See application file for complete search history.

(56) References Cited

U.S. PATENT DOCUMENTS

| | | | |
|---|---|---|---|
| 2011/0034902 A1* | 2/2011 | Markussen | A61M 5/3157 604/211 |
| 2013/0053790 A1 | 2/2013 | Karlsson | |
| 2013/0204198 A1* | 8/2013 | Burnell | A61M 5/2033 604/197 |

FOREIGN PATENT DOCUMENTS

| | | |
|---|---|---|
| JP | H08164206 A | 6/1996 |
| WO | 2003008023 | 1/2003 |
| WO | 2003080160 | 10/2003 |
| WO | 2005097233 | 10/2005 |
| WO | 2005097240 | 10/2005 |
| WO | 2008107813 | 9/2008 |
| WO | 2008133702 | 11/2008 |
| WO | 2011032731 | 3/2011 |
| WO | 2015007812 | 1/2015 |
| WO | 2015017550 | 2/2015 |
| WO | 2015101574 | 7/2015 |
| WO | 2016149014 | 9/2016 |

OTHER PUBLICATIONS

Written Opinion of the International Searching Authority pertaining to International Application No. PCT/US2018/029331; dated Aug. 6, 2018.

* cited by examiner

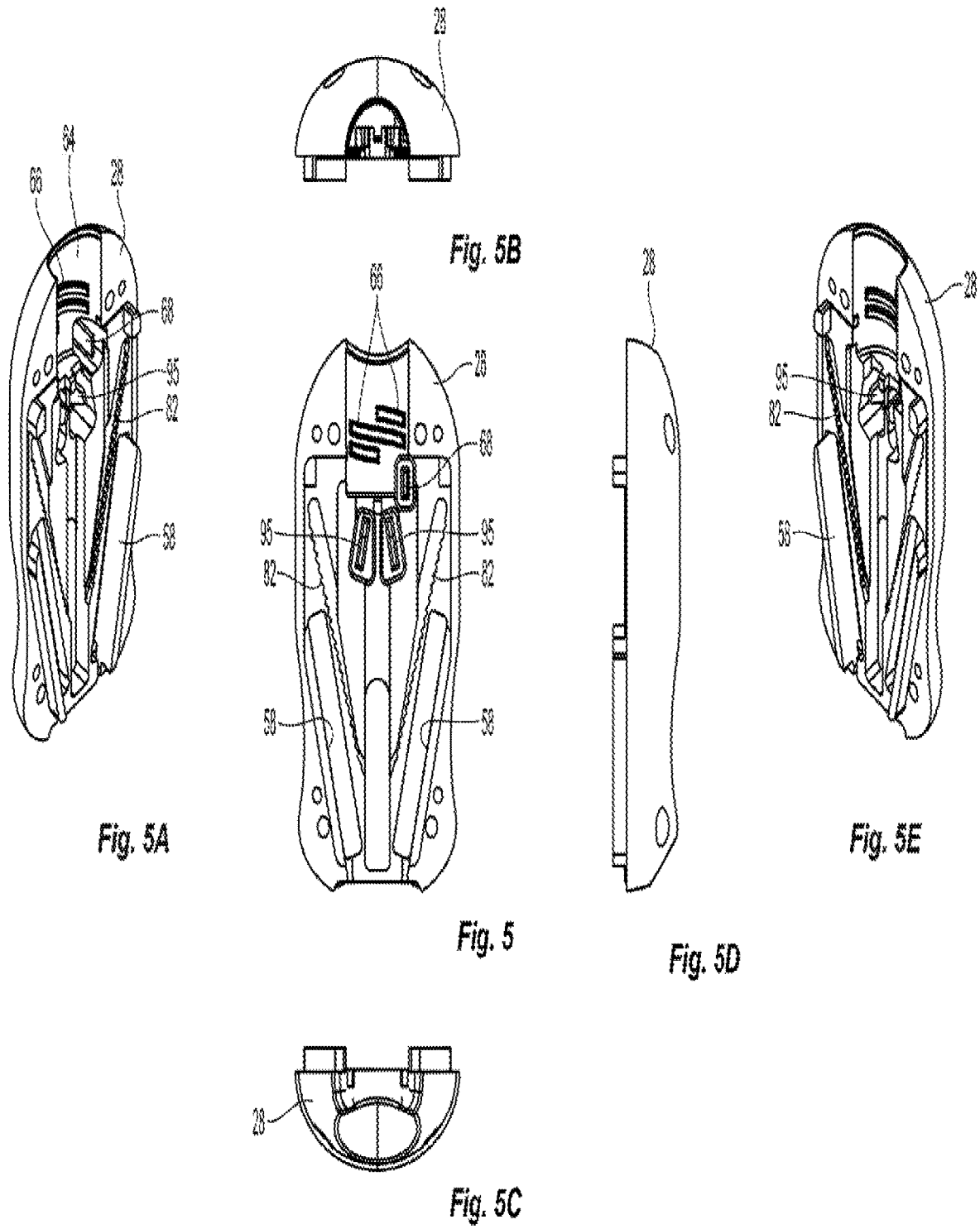

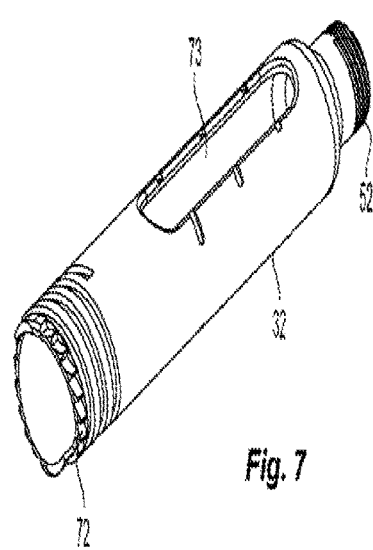
*Fig. 7*
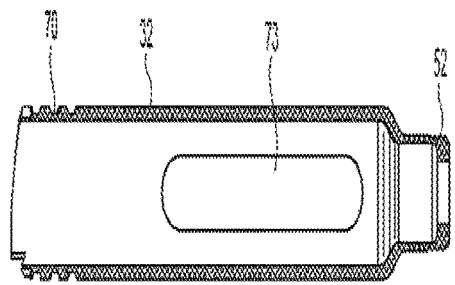
*Fig. 7C*
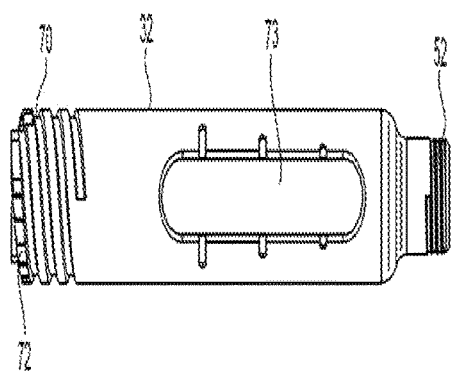
*Fig. 7A*
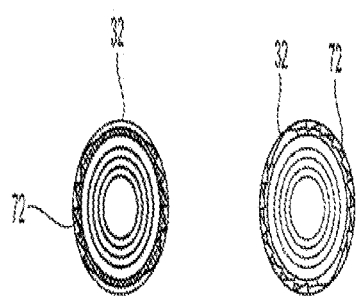  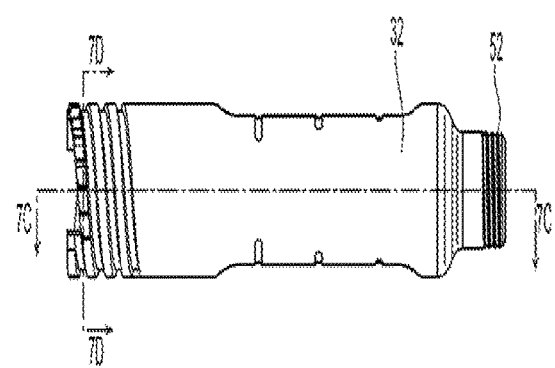 
*Fig. 7D*   *Fig. 7E*   *Fig. 7B*   *Fig. 7F*

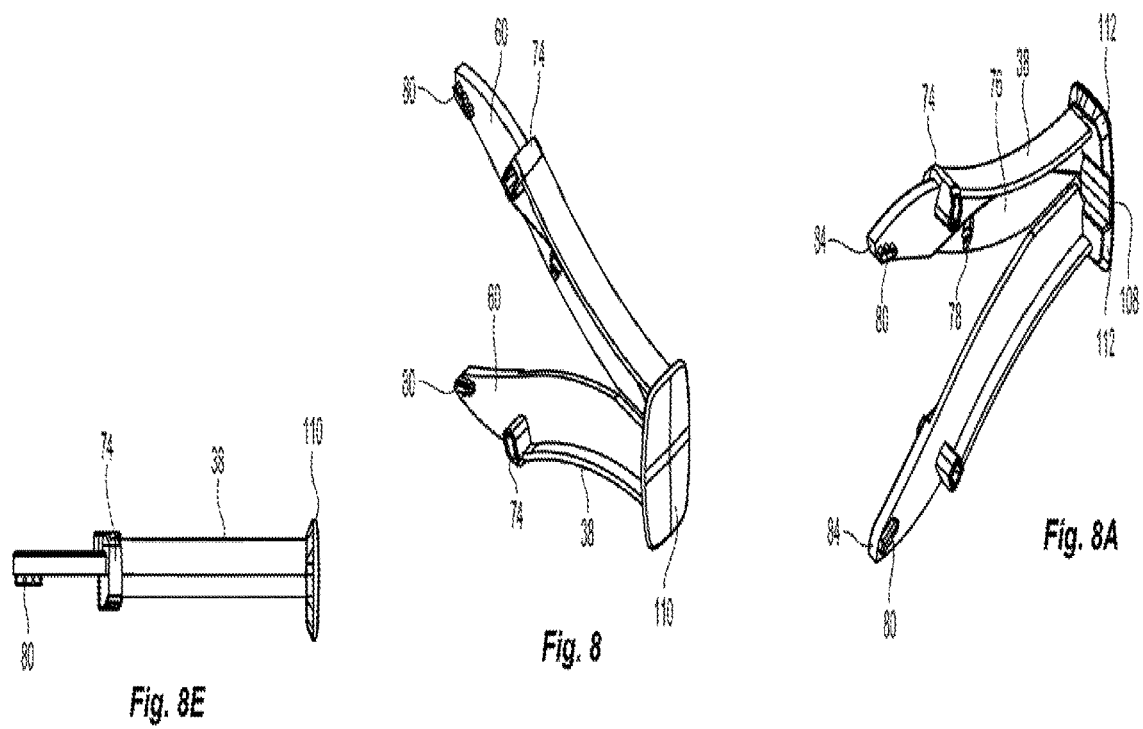
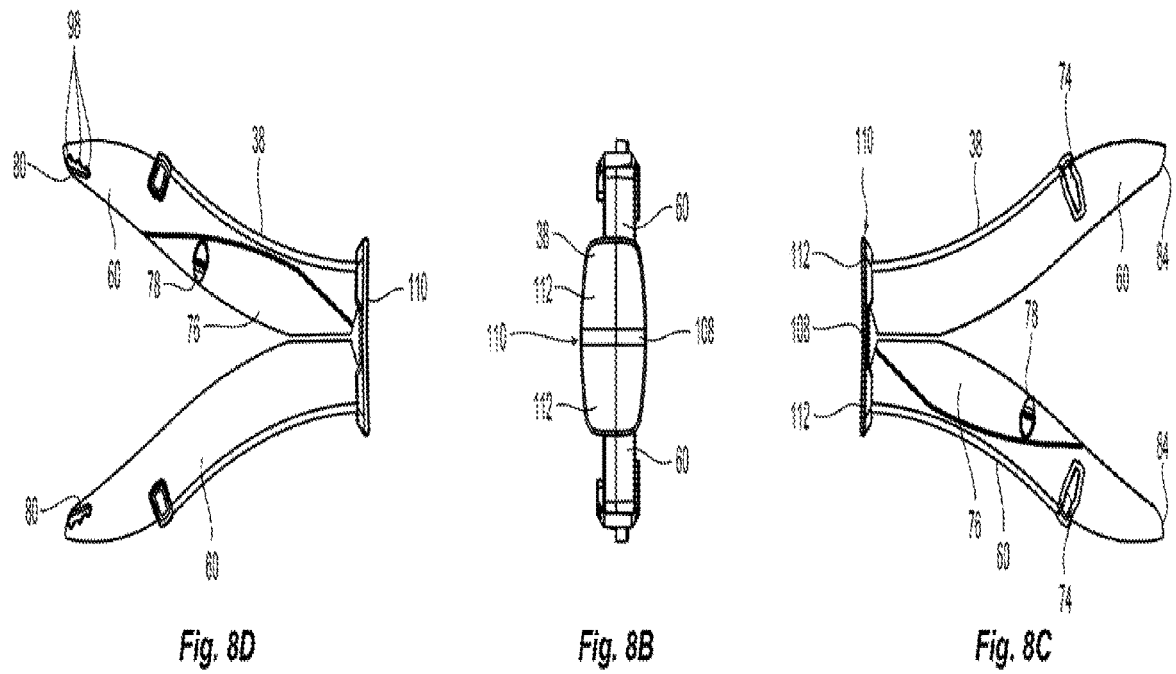

INJECTION DEVICE WITH PLUNGER ARRANGMENT AND CONVERGING RAMPS

CROSS REFERENCE TO RELATED APPLICATION

This application is a National Stage of International Application No. PCT/US2018/029331, filed Apr. 25, 2018, which claims priority to U.S. Provisional Patent Application Ser. No. 62/500,055, filed May 2, 2017, the disclosures of which are hereby expressly incorporated by reference herein in their entirety.

BACKGROUND

The present disclosure relates to medical delivery devices such as injection devices.

Conventional injection devices are often used to inject a medicament into patient. Such devices commonly employ a plunger or similar elongate rod to advance a piston to dispense the medicament. Such devices might be refillable wherein retraction of the piston is used to draw-in the medicament before the injection process, or, the device might be configured to be used with disposable containers that have been prefilled with the medicament.

For example, injection pens that receive disposable cartridges containing insulin are often used by diabetes patients. Such pens generally include an elongate rod that acts on a piston within the cartridge. As the rod advances the piston, the medicament within the cartridge is dispensed through a needle and into the patient.

Various other configurations are also known. For example, Judson, WO 2016/149014 A1, published Sep. 22, 2016, and U.S. provisional patent application Ser. No. 62/134,865 filed Mar. 18, 2015, the disclosures of both of which are incorporated herein by reference, disclose a dispensing device with a drive mechanism having converging ramps. The disclosed device includes a plunger having two separate plunger arms that are pivotally connected together at the button end that is pushed by the user to eject medicament. While the disclosed device is effective, improvements are desirable.

For example, some users are prone to push excessively hard on the plunger. Such user actions places greater pressures and stresses on the components of the device and is not the optimal method for discharging medicament from the device. It may also cause excessive wear or breakage of individual parts of the device. Improvements which address this issue are desirable. Furthermore, improvements that reduce the cost and complexity of manufacture while retaining or enhancing the functionality of the device are desirable.

SUMMARY

The present disclosure provides an enhanced injection device having a plunger that engages converging ramps.

In an illustrative embodiment, the injection device includes a braking mechanism that is engaged when the user exerts an excessive force on the plunger during an injection procedure.

In an illustrative embodiment, the injection device includes a one-piece plunger that improves manufacturing efficiency.

BRIEF DESCRIPTION OF THE DRAWINGS

The above mentioned and other features of this disclosure, and the manner of attaining them, will become more apparent and will be better understood by reference to the following description of embodiments of the invention taken in conjunction with the accompanying drawings, wherein:

FIG. 5 is a top view of a housing member.

FIG. 5A is a perspective view of the housing member of FIG. 5

FIG. 5B is an end view of the housing member of FIG. 5.

FIG. 5C is an end view of the housing member of FIG. 5.

FIG. 5D is a side view of the housing member of FIG. 5.

FIG. 5E is a perspective view of the housing member of FIG. 5.

FIG. 7 is a perspective view of a cartridge holder.

FIG. 7A is a side view of the cartridge holder.

FIG. 7B is another side view of the cartridge holder.

FIG. 7C is a cross sectional view taken along line 7C-7C of FIG. 7B.

FIG. 7D is a cross sectional view taken along line 7D-7D of FIG. 7B.

FIG. 7E is an end view of the cartridge holder.

FIG. 7F is another end view of the cartridge holder.

FIG. 8 is a perspective view of the plunger.

FIG. 8A is perspective view of the plunger.

FIG. 8B is an end view of the plunger.

FIG. 8C is a side view of the plunger.

FIG. 8D is a side view of the plunger.

FIG. 8E is a top view of the plunger.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
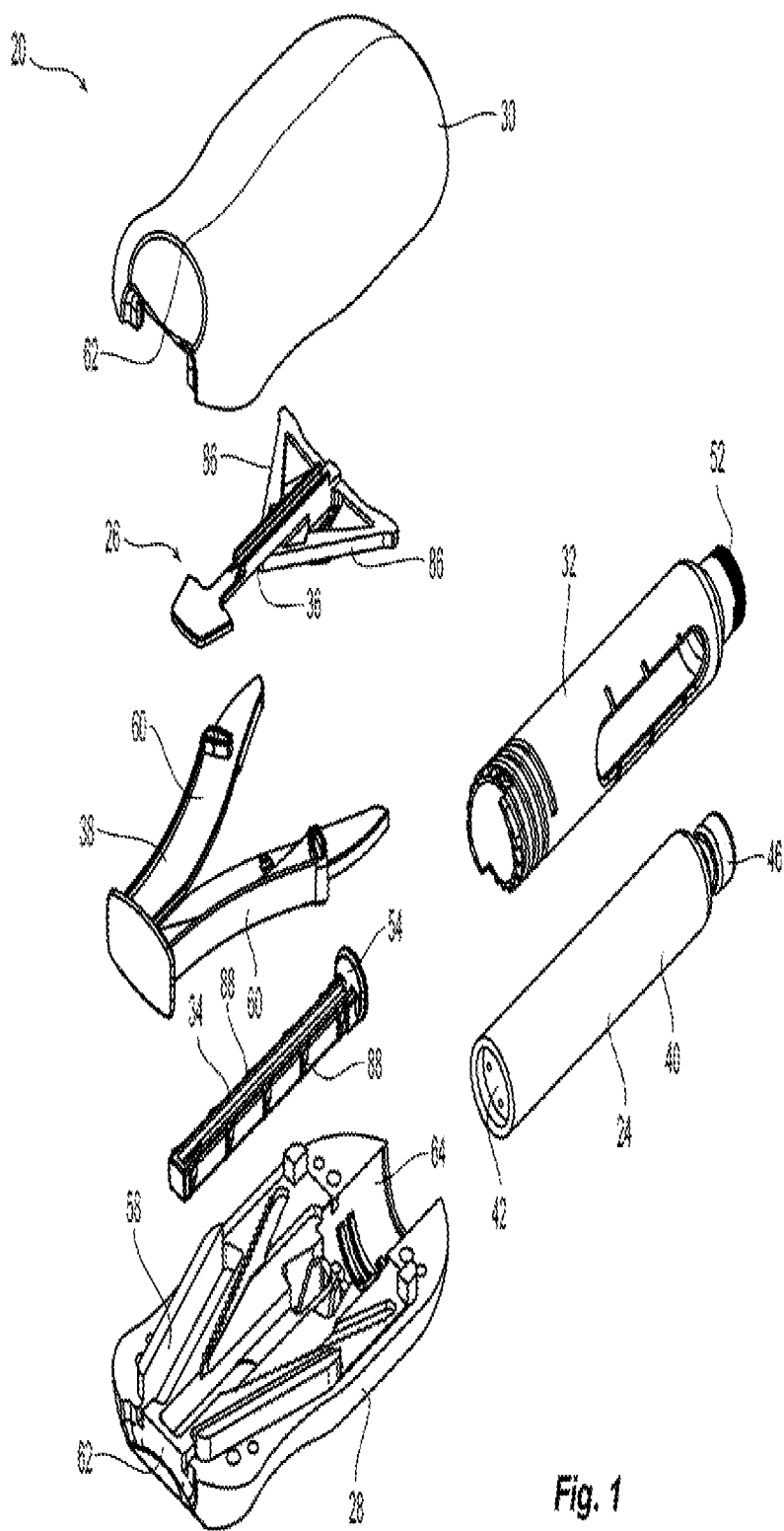
FIG. 1 is an exploded view of an injection device.
Figure 2C:
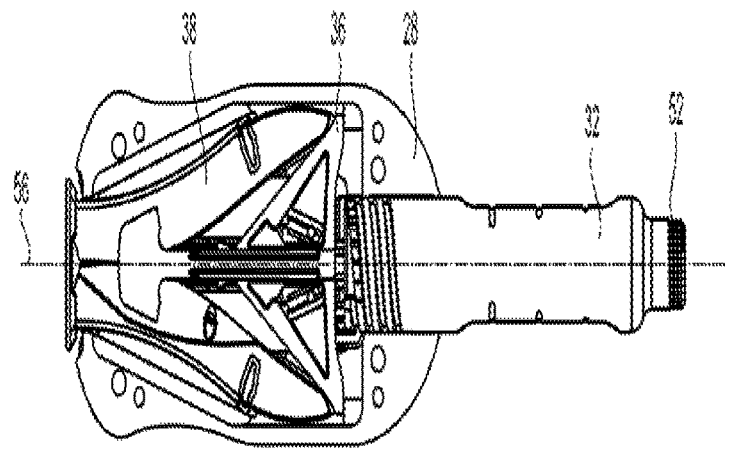
FIG. 2C is a top view of the injection device with the plunger in the advanced position with a housing member removed.
Figure 2A:
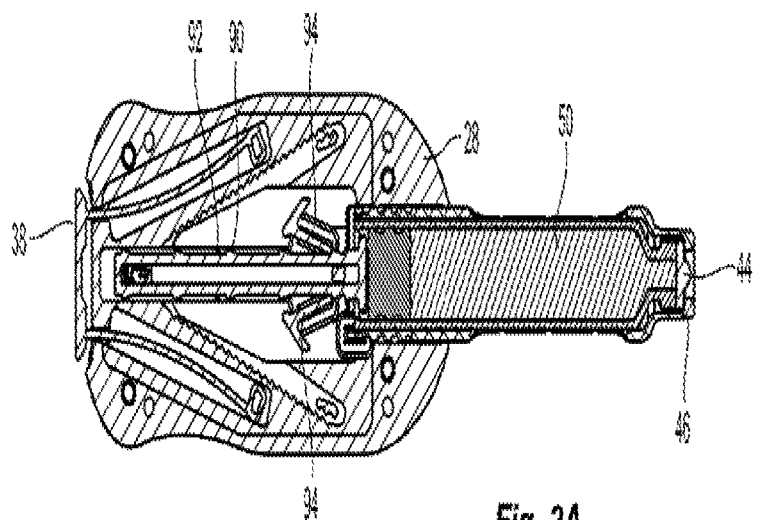
FIG. 2A is a cross sectional view taken along line 2A-2A of FIG. 2.
Figure 2B:
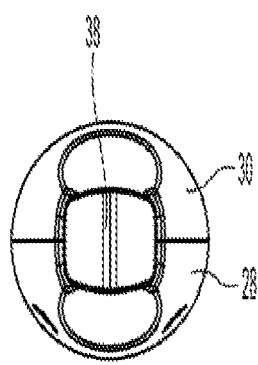
FIG. 2B is an end view of the device of FIG. 2.
Figure 2:
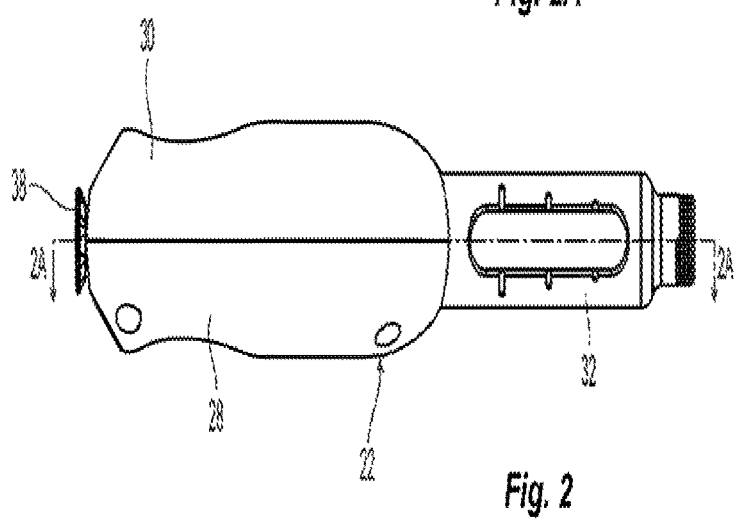
FIG. 2 is a side view of the injection device with the plunger in the advanced position.

An exemplary medication dispensing device 20 is shown in FIG. 1. Device 20 includes a housing assembly 22 which secures a medicament cartridge 24 to the device, and a drive assembly 26. The housing assembly 22 includes first and second housing members 28, 30 and a cartridge holder 32 which is also referred to herein as a cartridge retainer. The driving assembly 26 includes a drive stem 34, a driver 36 and a plunger 38.

Figure 3C:
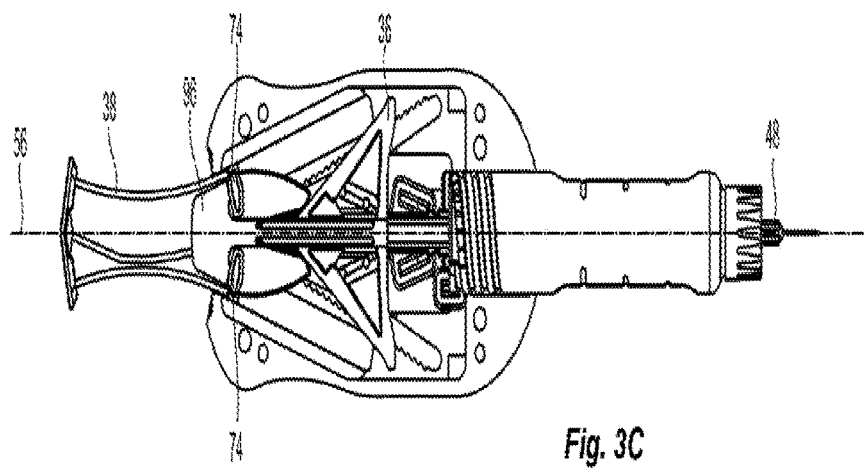
FIG. 3C is a top view of the injection device with the plunger in the retracted position with a housing member removed.
Figure 3A:
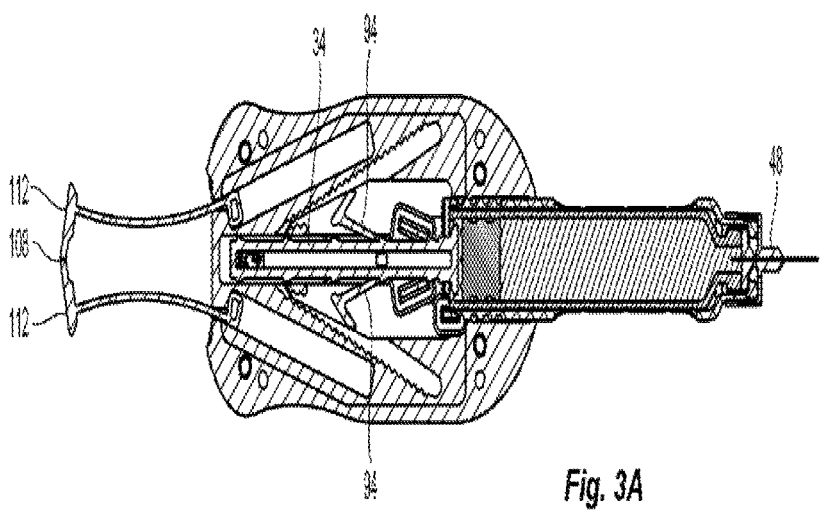
FIG. 3A is a cross sectional view taken along line 3A-3A of FIG. 3.
Figure 3B:
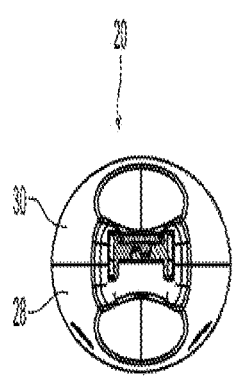
FIG. 3B is a cross sectional view taken along line 3B-3B of FIG. 3.
Figure 3:
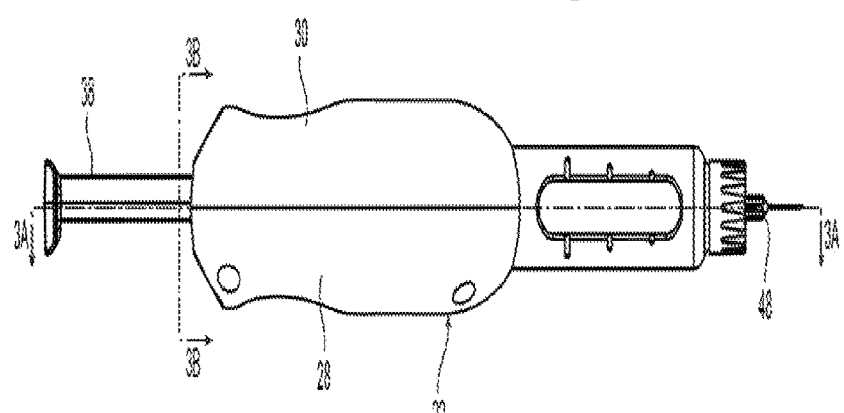
FIG. 3 is a side view of the injection device with the plunger in the retracted position.
Figure 4C:
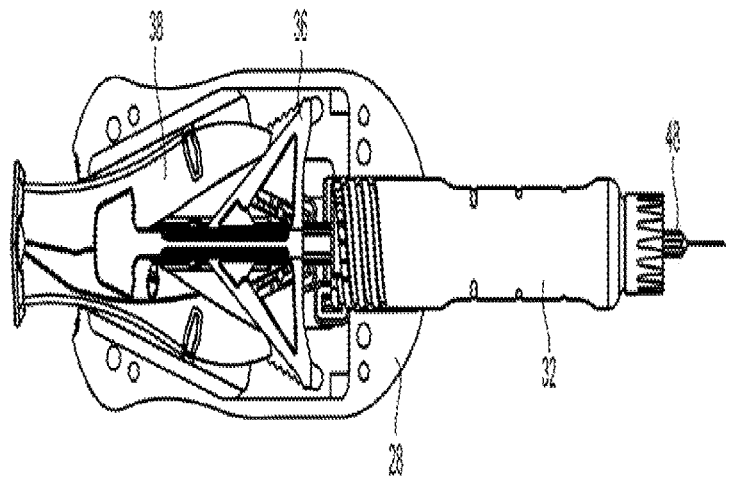
FIG. 4C is a top view of the injection device with the plunger in a partially advanced position with a housing member removed.
Figure 4A:
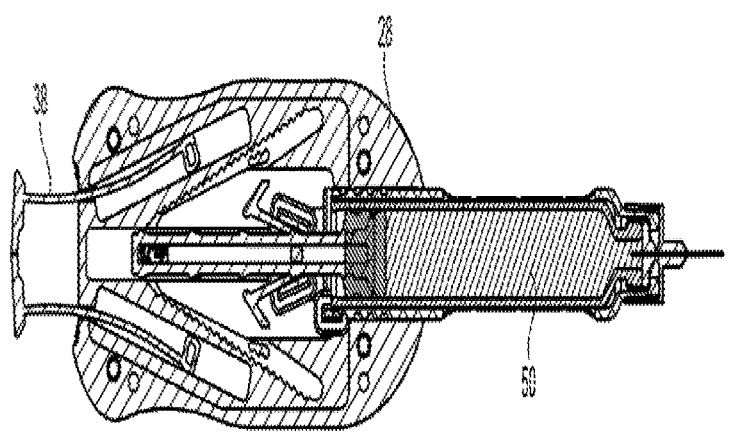
FIG. 4A is a cross sectional view taken along line 4A-4A of FIG. 4.
Figure 4B:
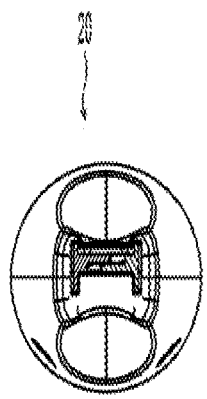
FIG. 4B is a cross sectional view taken along line 4B-4B of FIG. 4.
Figure 4:
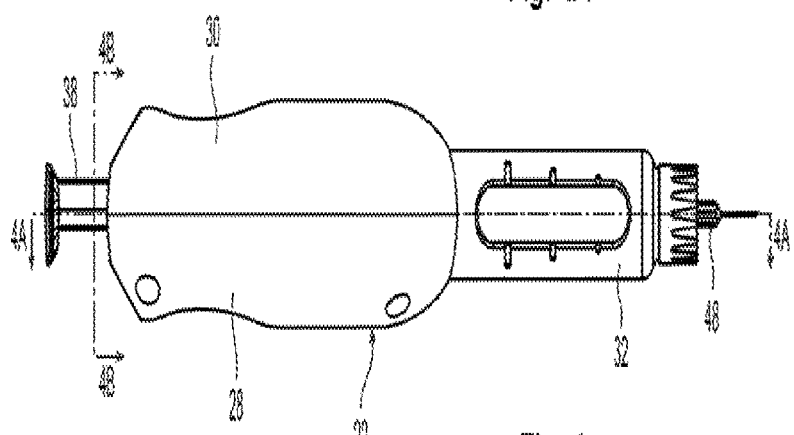
FIG. 4 is a side view of the injection device with the plunger in a partially advanced position.
Figure 6A:
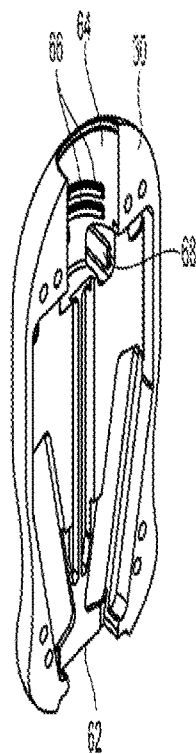
FIG. 6A is a perspective view of the housing member of FIG. 6.
Figure 6B:
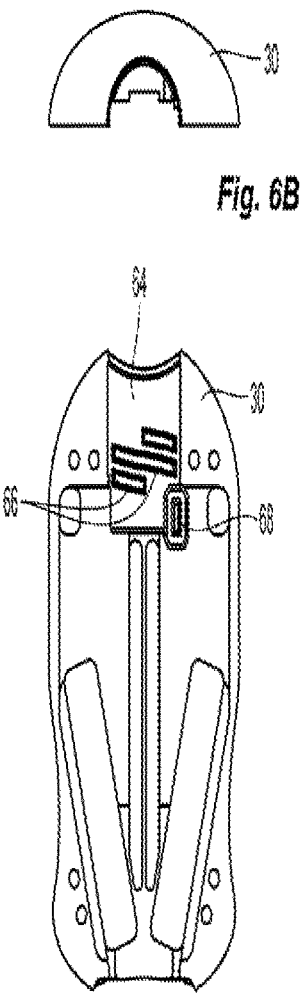
FIG. 6B is an end view of the housing member of FIG. 6.
Figure 6:
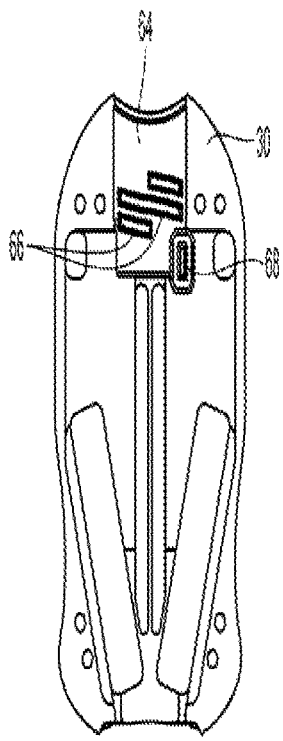
FIG. 6 is a top view of another housing member.
Figure 6D:
FIG. 6D is a side view of the housing member of FIG. 6.
Figure 6E:
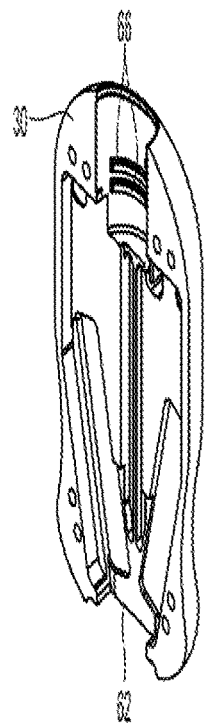
FIG. 6E is a perspective view of the housing member of FIG. 6.
Figure 6C:
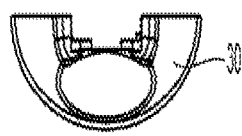
FIG. 6C is an end view of the housing member of FIG. 6.

As best seen in FIG. 3A, cartridge 24 is a conventional medicament cartridge including a barrel 40 with an interior reservoir sealed at one end by a slidable piston 42 and sealed at the other end by a septum 44 held by a crimp ring 46. A needle assembly 48 is mounted to an externally threaded end 52 of cartridge retainer 32 and pierces the septum 44 to provide an outlet during dispensing of the medication 50 filling the barrel reservoir. A removable cap (not shown) may be used to cover the needle assembly when device 20 is not in use. Cartridge 24 may hold multiple doses of medicine, or a single dose, depending on the design of device 20. The shown device 20 is a multiple use, fixed dose device, meaning that the device may be used to deliver the same dose on multiple occasions from a single cartridge 24. The shown cartridge is merely one exemplary form of container from which the drive assembly 26 may force an emptying thereof, as, for example, a container that is compressed by action of the drive assembly alternatively may be employed.

Drive stem 34 of drive assembly 26 projects into barrel 40 and has a foot 54 that engages piston 42. As drive stem 34 is advanced along drive axis 56, foot 54 advances piston 42 within barrel 40 to discharge medication 50 from needle assembly 48. As further discussed below, the advancement of plunger 38 biases driver 36 forward along axis 56 to thereby advance drive stem 34 into engagement with piston 42 when the device is being used to discharge medication.

Driver 36 directly engages drive stem 34 and is constrained by interior surfaces of housing assembly 22 to be axially translatable and rotatably fixed therein. The interaction of converging ramp surfaces 58 located on the interior surfaces of housing assembly 22 and plunger arms 60 provides a mechanical advantage allowing the user to depress the plunger and discharge the medicament using less force than would otherwise be required if the device did not provide a mechanical advantage.

Housing members 28, 30 are shown in greater detail in FIGS. 5, 5A-5E and FIGS. 6, 6A-6E. The housing members 28, 30 are secured together and capture driver 36 and plunger 38 therebetween while still permitting relative movement of these components. The housing members 28, 30 may be secured together with adhesive, threaded fasteners, snap-fit connections or other suitable means.

Housing members 28, 30 have a cylindrical opening 64 at one end which includes thread members 66. Each of the illustrated housing members also includes a ratchet member 68 located in or adjacent the cylindrical opening 64. Cartridge retainer 32 includes spiral grooves 70 and ratchet teeth 72 on the end which engages housing members 28, 30. Grooves 70 define double-start spiral grooves which receive thread members 66. Ratchet teeth 72 are located on spiral lands between grooves 70. Interaction between ratchet members 68 and ratchet teeth 72 allow cartridge retainer 32 to be rotated inwardly into the cylindrical opening 64 but prevent retainer 32 from being rotated back out. To detach cartridge retainer 32, and the cartridge 24 located therein, from housing members 28, 30, housing members 28, 30 must be separated. Device 20 may be a single use dispenser intended to be disposed of after emptying the initial cartridge 24. For such single use dispensers, housing members 28, 30 may be permanently secured together. Alternatively, threaded fasteners or other suitable attachment means may be employed to allow housing members 28, 30 to be detached from each other and re-secured by the user to thereby allow the user to replace an empty cartridge 24 with a full cartridge.

In one embodiment, cartridge retainer 32 and housing members 28, 30 are configured to facilitate the initial priming of cartridge 24. For example, device 20 is shipped with a full cartridge 24 located within retainer 32 and with retainer 32 not fully rotated into its final position. Before the first injection, the user rotates cartridge retainer 32 until thread members 66 hit the end of spiral grooves 70 which blocks or prevents the further rotation of retainer 32. As retainer 32 is twisted into its installed position, it moves cartridge 24 toward foot 54 of drive stem 34. Drive stem 34 may be positioned so that this twisting of cartridge retainer 32 into its installed position biases piston 42 forward a small amount to thereby prime cartridge 24 for its first dispensing of medicine 50. In one embodiment, needle assembly 48 is mounted so that it pierces septum 44 and is ready to dispel air located in the needle assembly and dispense a small amount of medicine before cartridge retainer 32 is twisted into its final position if the securement of cartridge retainer 32 is going to be used to prime cartridge 24.

Window 73 in cartridge retainer 32 allows a user to view cartridge 24 and thus, visually determine the quantity of medicine remaining in cartridge 24 provided that barrel 40 is transparent or at least partially transparent. Window 73 may also be positioned such that when cartridge 32 is disposed in its installed position it assumes a predefined position relative to housing assembly 22 to thereby provide the user with confirmation that cartridge retainer 32 is in its proper installed position.

The priming of cartridge 24 by the rotation of cartridge retainer 32 relative to housing members 28, 30 is also discussed in U.S. provisional application Ser. No. 62/500, 004, filed May 2, 2017 and entitled INJECTION DEVICE WITH PRIMING ARRANGEMENT filed by the same Applicant as the present application, the disclosure of which is incorporated herein by reference. Various other cartridge retainer structures, which do not necessarily include a priming function, may alternatively be employed with the device of the present application. For example, WO 2016/149014 A1 discloses one example of such an alternative cartridge retainer.

Plunger 38 projects from housing assembly 22 opposite cartridge retainer 32 whereby the user may retract plunger 38 by pulling it outwardly from housing assembly 22 to place device 20 in condition for an injection procedure and push plunger 38 into housing assembly 22 to cause the injection procedure. Each of the housing members 28, 30 define a portion of the opening 62 through which plunger 38 projects. The housing member 28 also defines ramp surfaces 58. Ramp surfaces 58 constrain the outward movement of plunger arms 60 as plunger 38 is advanced toward needle assembly 48.

Plunger 38 is shown in detail in FIGS. 8, 8A-8E. Each of the plunger arms 60 include a slide member 74. Each of the slide members 74 slide along one of the ramp surfaces 58 as plunger 38 is advanced within housing assembly 22. The inner portions of plunger arms 60 includes a recessed area 76 that allows the recessed areas 76 of both arms to overlap as arms 60 are biased toward each other as plunger 38 is pulled out of housing assembly 22 in a manner similar to the way the blades of a pair of scissors overlap when the scissors are closed. Detents 78 are located in recessed areas 76 of each plunger arm. Detents 78 engage each other when plunger 38 is retracted from housing assembly 22 in preparation for an injection to thereby hold plunger 38 in the retracted position. When the user begins pushing plunger 38 into housing assembly 22 to initiate an injection, the force applied by the user will first disengage detents and then begin advancing plunger 38. The force required to overcome the attachment of detents 78 is relatively light as further discussed below.

As plunger 38 is advanced, an engagement surface 84 proximate the forward tip of plunger arms 60 engages inclined surfaces 86 of driver 36. In the illustrated embodiment, the gap between ramp surfaces 58 and inclined surfaces 86 is insufficient to allow plunger arms 60 to pass therebetween, thus, as slide member 74 advances along ramp surface 58 engagement surfaces 84 on arms 60 will exert a force on inclined surfaces 86 and push driver 36 forward toward needle assembly 48. In this regard it is noted that inclined surfaces 86 and ramp surfaces 58 are not parallel and thus engagement surfaces 84 slide along inclined surfaces 86 until they begin to push driver 36 forward and as the plunger arms 60 advance, engagement surfaces 84 both slide along and push inclined surfaces 86.

Drive stem 34 includes a plurality of ratchet teeth 88 encircling the central stem of drive stem 34. The surface 90 of ratchet teeth 88 facing needle assembly 48 are inclined while the opposite side of teeth 88 define a stop surface 92 extending perpendicular to axis 56. Driver 36 includes two pawl members 94 that engage drive stem 34 and is illustrated in FIG. 3A. As driver 36 is advanced by plunger arms 60, pawl members 94 engage one of the stop surfaces 92 on drive stem 34 and push drive stem 34 forward whereby foot 54 pushes piston 42 forward and causes medication 50 to be discharged through needle assembly 48.

When plunger 38 is retracted, slide members 74 engage retraction head 96 and pull driver 36 rearwardly during the final phase of the retraction (see FIG. 3C). As driver 36 is retracted, pawls 94 slide along drive stem 34. When pawls 94 encounter a ratchet tooth 88, the inclined surface 90 of the ratchet tooth allows pawls 94 to slide over the ratchet tooth 88.

Housing member 28 includes two ratchet members 95 (FIG. 5) that engage drive stem 34 and block or prevent the retraction of drive stem 34 when plunger 38 is being retracted. Ratchet members 95 have a sloped surface that allows drive stem 34 to be advanced toward needle assembly 48 as illustrated in FIGS. 5A and 5E.

Each of the plunger arms 60 also includes a braking member 80 and housing member 28 includes a pair of braking tracks 82. As slide members 74 travel along ramps 58 braking members 80 will remain spaced apart from braking track 82 in both the forward and rearward directions so long as the force applied by the user to button end 110 of plunger 38 during advancement of the plunger is not excessive. Braking tracks 82 are offset from the path braking member 80 follows when slide members 74 travel along ramps 58 and both tracks 82 and ramps 58 are disposed on the same housing member 28 in the illustrated embodiment. When the user applies an excessive force to button end 110 of plunger 38 when advancing plunger 38 into housing assembly 22, the excessive force will bias braking members 80 into braking track 82 to thereby increase the resistance to the force being applied by the user. The illustrative braking member 80 and braking track 82 include undulations or teeth that will engage and disengage as braking member 80 advances along braking track 82 causing an audible chatter and also causing the user to feel a resistance force that includes repetitive increases or spikes in resistance as the individual teeth of braking member 80 and braking track 82 engage and then release.

Figure 9:
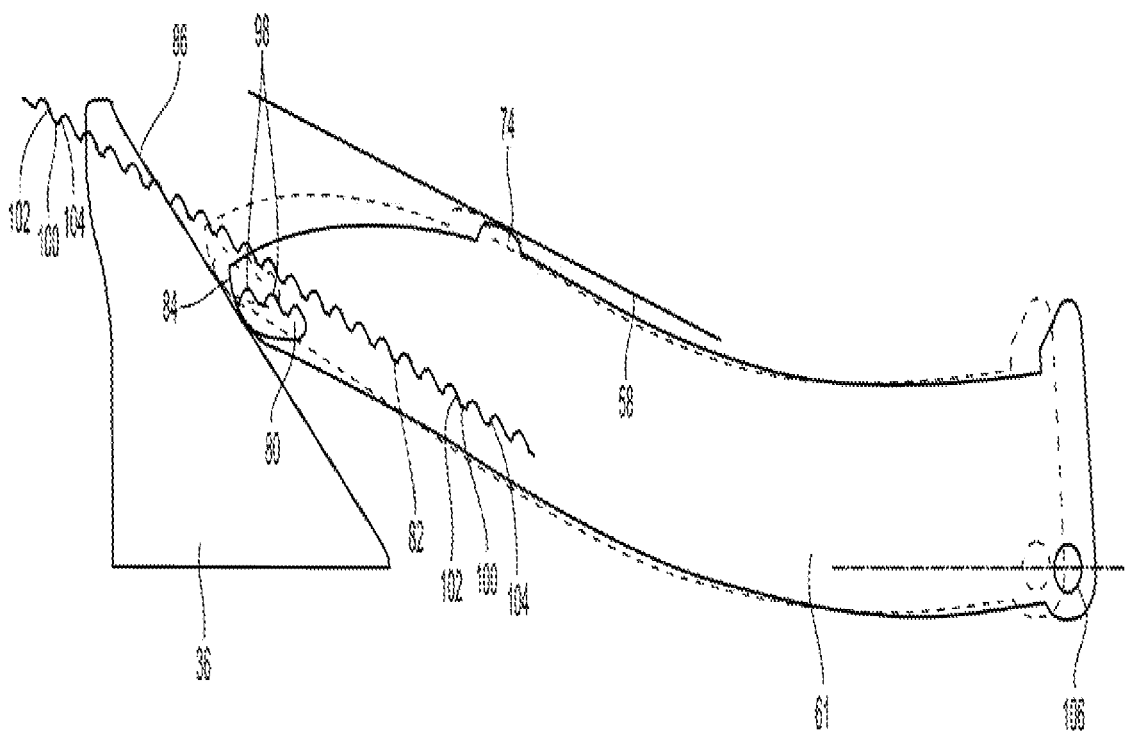
FIG. 9 is a schematic view depicting the advancement of a plunger arm.

FIG. 9 provides an enlarged view illustrating the operation of brake member 80 and braking track 82. FIG. 9 illustrates a plunger arm 61 that is similar to plunger arms 60 but is part of a plunger assembly having two separate plunger arms 61 that are pivotally connected together instead of both arms being part of a single integrally formed part.

In FIG. 9, plunger arm 61 is illustrated in both solid lines and in dashed lines. When the plunger is being pushed inwardly by the user using an appropriate amount of force, slide member 74 will be engaged with ramp 58 and engagement surface 84 of arm 61 will be engaged with surface 86 on driver 36 while braking member 80 is spaced from braking track 82. When the user pushes the plunger with an excessive amount of force, plunger arm 61 will begin to bow or flex as indicated by the dashed lines in FIG. 9. In this bowed condition, braking member 80 will be brought into contact with braking track 82.

It is noted that the threshold force required to flex the plunger arms may be calculated and the materials and cross sectional profile of the plunger arms may be selected such that the arms will flex the required amount to bring the braking member into contact with the braking track at a threshold force that corresponds to the upper limit of the recommended force to be applied to the plunger for advancement of the piston in cartridge 24.

Braking member 80 includes a plurality of teeth 98 that face braking track 82. Braking track 82 includes a plurality of teeth 100. When brake member 80 engages track 82, the teeth 98 engage teeth 100 and slide along track 82 with a series of impacts as teeth 98 impact teeth 100 and then release and engage the next set of teeth 100 on track 82.

As plunger arm 61 is pushed forward with braking member 80 in engagement with braking track 82, this engagement will increase the resistance felt by the user and also create "chatter" as the teeth on braking member 80 pass over the teeth 100 on braking track 82. This chatter may be felt by the user and it will also create an audible sound that may be heard by the user.

In the illustrated embodiment, teeth 100 have an inclined slide surface 102 that facilitates the sliding of teeth 98 in a rearward direction and impact surfaces 104 that are positioned nearly perpendicular to the direction of travel of teeth 98 to resist the forward movement of teeth 98 and, thus, of plunger 38. Both the increased resistance of forward movement of plunger 38 and the chatter caused by the series of impactful engagements of teeth 98 with teeth 100 will alert the user that they are pressing on plunger 38 in an excessively forcible manner and that they should lessen the force being applied to plunger 38. The increased resistance will slightly slow the forward advancement of plunger 38 even if the user does not less the force being applied, however, this will generally be a secondary consideration with the primary purpose of brake member 80 and braking track 82 being to alert the user that an excessive force is being applied. Alternative embodiments, however, utilize a similar braking mechanism for the primary purpose of slowing the movement instead of alerting the user.

Figure 9A:
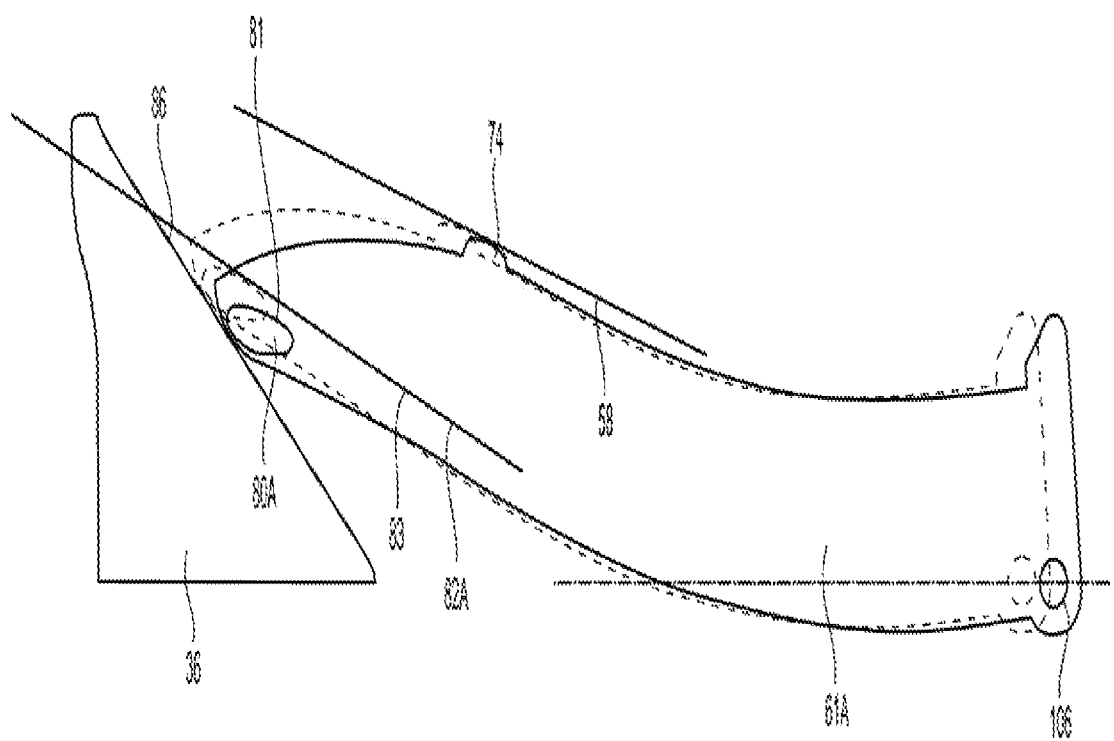
FIG. 9A is a schematic view depicting the advancement of an alternative plunger arm.

FIG. 9A discloses alternative embodiment of the plunger arm. Plunger arm 61A shown in FIG. 9A is similar to plunger arm 61 shown in FIG. 9 but the braking member 80A does not include teeth on frictional engagement surface 81. Another difference is that braking track 82A includes a frictional engagement surface 83 instead of teeth. In FIG. 9A, the solid lines show plunger arm 61A when an appropriate amount of force is being applied to the plunger by the user and the dashed lines show the plunger arm in a bowed condition caused by excessive force. The application of excessive force brings braking member 80A into contact with braking track 82A.

One or both of frictional engagement surfaces 81 and 83 may include a surface layer of material that enhances the frictional resistance to sliding between surfaces 81 and 83. These surfaces may also be provided with a texture that enhances frictional resistance or generates an audible noise when the two surfaces are in sliding engagement. Similar to the embodiment of FIG. 9, the embodiment of FIG. 9A both increases the resistance to forward movement and alerts the user, due to the enhanced resistance, when the user employs excessive force on the plunger.

It is also noted that arms 61, 61A each have an opening 106 for receiving a pin to pivotally couple the arm with another arm. In one embodiment, the pin is located on the opposing arm, or the opposing arm also includes an opening with a third part defining a pin or pins for pivotally engaging the opening in both arms to thereby form the plunger.

In contrast to arms 61, 61A, arms 60 of plunger 38 are part of the same integral part and are connected together via material bridge 108. Material bridge 108 forms the central portion of button end 110 of plunger 38 and connects the two opposing halves 112 of button end 110.

Material bridge 108 is thinner than the two opposing halves 112 of button end 110 and is sufficiently thin to flex as plunger 38 is moved along axis 56. Plunger 38 is a single molded part and the original molded configuration of plunger 38 is the configuration shown in FIGS. 8C and 8D. In this configuration, opposing arms 60 are spread apart. Arms 60 are slightly biased together when assembled into housing assembly 22 in the fully advanced position. FIGS. 2, 2A-2C show plunger 38 in the fully advanced position. As plunger 38 is retracted outwardly from housing assembly 22, arms 60 are further biased toward each other. Material bridge 108 flexes as arms 60 move toward and away from each other. In the illustrated embodiment, however, the stress applied to material bridge 108 during the range of movement resulting from normal operation of device 20 does not reach the yield stress of the material forming material bridge 108. As a result, material bridge 108 exerts a biasing force that seeks to place arms 60 in the configuration shown in FIGS. 2, 2A-2C.

When plunger 38 is at least partially retracted from housing assembly 22, the biasing force exerted by material bridge 108 will tend to draw plunger 38 back into housing assembly 22. FIGS. 4, 4A-4C show plunger 38 in a partially retracted position while FIGS. 3, 3A-3C show plunger 38 in a fully retracted position. When plunger 38 is fully retracted by the user when preparing for an injection event, it is desirable for plunger 38 to remain in the fully retracted position (FIGS. 3, 3A-3C), until after the user has inserted the needle into the injection site and is ready to begin the injection. Detents 78 on arms 60 engage with each other to retain arms 60 in the fully retracted position.

Advantageously, in the exemplary embodiment the force required to disengage detents 78 is only slightly greater than the biasing force generated by material bridge 108 so that the user is not required to exert a significant force to separate detents 78. As the user depresses plunger 38 to cause the injection, the biasing force generate by material bridge 108 will assist the user.

Use of a material bridge allows plunger 38 to be formed out of a single molded part instead of two or more parts. For example, the plunger arms of FIGS. 9 and 9A which are pivotally connected to another plunger arm require at least two parts to form the plunger. The use of a single molded part reduces parts inventory and the assembly labor required to manufacture device 20 thereby enhancing manufacturing efficiency.

Alternative embodiments of a molded one part plunger employ a button end where the material bridge of the button end is stressed beyond the yield point without fracturing the material whereby the material bridge does not exert a biasing force on arms 60. In such an embodiment, the material bridge may function as a living hinge.

Device 20 may further comprise a medication or drug. In one embodiment, a system may comprise one or more devices including device 20 and a drug. The term drug or medication refers to one or more therapeutic agents including but not limited to insulins, insulin analogs such as insulin lispro or insulin glargine, insulin derivatives, glucagon-like peptide (GLP-1) receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies and any therapeutic agent that is capable of delivery by device 20. The drug as used in device 20 may be formulated with one or more excipients. Device 20 is operated in a manner generally as described above by a patient, caregiver or healthcare professional to deliver drug to a person.

While this invention has been described as having exemplary designs, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An injection device comprising:
   a housing assembly defining a pair of ramps and adapted to hold a medicament cartridge, wherein the cartridge defines a container for a medication and has a first end adapted to receive a needle assembly and a piston disposed opposite the needle assembly wherein, during use, advancement of the piston within the cartridge ejects medication from the needle assembly;
   a driver operably coupled with the piston and adapted to advance the piston within the cartridge;
   a plunger having a pair of arms, the plunger being moveable between a retracted position and an advanced position by a force exerted on the plunger, each of the arms being engageable with a respective one of the ramps whereby when the plunger is moved from the retracted position to the advanced position, the movement of the arms is guided by the ramps and the plunger moves the driver to thereby advance the piston; and
   a braking mechanism including a braking member disposed on at least one of the arms and a braking track disposed on the housing assembly proximate the ramp engaged by the at least one arm wherein, when the force exerted on the plunger exceeds a threshold value and causes the arms to flex, flexure of the at least one arm engages the braking member with the braking track, wherein the engagement of the braking member with the braking track increases the resistance of the plunger to the force being exerted thereon.

2. The injection device of claim 1 wherein when the plunger is moved from the advanced position to the retracted position the arms are biased toward each other.

3. The injection device of claim 1 wherein the engagement of the braking member with the braking track generates an audible noise as the plunger advances.

4. The injection device of claim 1 wherein the braking track is offset from a path followed by the braking member when the arm is engaged with the ramp.

5. The injection device of claim 1 wherein the braking mechanism includes a pair of braking members, each plunger arm includes a braking member of the pair of braking members, and the device includes a pair of braking tracks, each of the braking tracks being disposed proximate the respective one of the ramps whereby, when the force exerted on the plunger exceeds the threshold value and causes the arms to flex, flexure of the arms engage the braking members with the braking tracks.

6. The injection device of claim 5 wherein the engagement of the braking members with the braking tracks increases the resistance of the plunger to the force being exerted thereon.

7. The injection device of claim 6 wherein the engagement of the braking members with the braking tracks generates an audible noise as the plunger advances.

8. The injection device of claim 7 wherein each of the braking tracks are offset from a path followed by a respective one of the braking members when the arms are engaged with the ramps.

9. The injection device of claim 1 wherein the plunger arms are connected together by a material bridge, the material bridge flexing as the arms move relative to each other and wherein the material bridge biases the plunger arms apart from each other.

10. The injection device of claim 9 wherein a biasing force exerted by the material bridge biases the plunger towards the advanced position.

11. The injection device of claim 10 wherein each of the arms define a detent, the detents being engageable when the plunger is in the retracted position and wherein the engaged detents prevent the material bridge from biasing the plunger toward the advanced position.

12. The injection device of claim 1, further including the medication contained in the cartridge.

13. An injection device comprising:

a housing assembly defining a pair of ramps and adapted to hold a medicament cartridge, wherein the cartridge defines a container for a medication, has a first end adapted to receive a needle assembly and a piston disposed opposite the needle assembly wherein, during use, advancement of the piston within the cartridge ejects medication from the needle assembly;

a driver operably coupled with the piston and adapted to advance the piston within the cartridge;

a plunger having a pair of arms, the plunger being moveable between a retracted position wherein the plunger extends from the housing assembly and the arms are positioned proximate each other and an advanced position wherein the plunger projects into the housing assembly and the arms are positioned apart from each other, each of the arms being engageable with a respective one of the ramps whereby when the plunger is moved from the retracted position to the advanced position, the movement of the arms is guided by the ramps and the plunger moves the driver to thereby advance the piston; and wherein the plunger arms are connected together by a material bridge, the material bridge flexing as the arms move relative to each other and wherein the material bridge biases the plunger arms apart from each other.

14. The injection device of claim 13 wherein the biasing force exerted by the material bridge biases the plunger towards the advanced position.

15. The injection device of claim 14 wherein each of the arms define a detent, the detents being engageable when the plunger is in the retracted position and wherein the engaged detents prevent the material bridge from biasing the plunger toward the advanced position.

16. The injection device of claim 13, further including the medication contained in the cartridge.

* * * * *